(12) United States Patent
Wilkinson et al.

(10) Patent No.: US 7,410,476 B2
(45) Date of Patent: *Aug. 12, 2008

(54) METHOD AND DEVICE FOR INTRADERMALLY DELIVERING A SUBSTANCE

(75) Inventors: Bradley M. Wilkinson, North Haledon, NJ (US); Mark Newby, Tuxedo, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 363 days.

This patent is subject to a terminal disclaimer.

(21) Appl. No.: 11/178,057

(22) Filed: Jul. 8, 2005

(65) Prior Publication Data

US 2005/0245877 A1 Nov. 3, 2005

Related U.S. Application Data

(63) Continuation of application No. 10/112,933, filed on Apr. 2, 2002, now Pat. No. 7,115,108.

(51) Int. Cl.
*A61M 31/00* (2006.01)
(52) U.S. Cl. ............... 604/93.01; 604/132; 604/173; 604/180

(58) Field of Classification Search .................. 604/11, 604/20, 22, 131, 132, 133, 141, 173, 174, 604/180, 890.1, 93.01, 212, 213, 214, 215, 604/216, 217, 237, 246, 272, 273, 274, 288, 604/156, 46, 47, 247, 891.1
See application file for complete search history.

(56) References Cited

U.S. PATENT DOCUMENTS

| 3,814,097 | A | * | 6/1974 | Ganderton et al. | .......... | 604/304 |
| 5,106,374 | A | * | 4/1992 | Apperson et al. | .......... | 604/140 |
| 5,921,962 | A | * | 7/1999 | Kriesel et al. | .............. | 604/132 |

* cited by examiner

*Primary Examiner*—Nicholas D. Lucchesi
*Assistant Examiner*—Aarti Bhatia
(74) *Attorney, Agent, or Firm*—Robert E. West

(57) ABSTRACT

A device for delivering a substance into the skin of a patient includes a body and a skin penetrating device having at least one skin penetrating member, such as a microneedle. The body includes an internal cavity and a device for indicating the delivery of a sufficient amount of the substance to the patient and for producing a dispensing pressure to dispense and deliver the substance from the cavity. The indicating device is visible from the exterior of the delivery device. In some embodiments, the indicating device is an elastic expandable diaphragm which, when the cavity is filled with a substance, creates the dispensing pressure.

16 Claims, 5 Drawing Sheets

METHOD AND DEVICE FOR INTRADERMALLY DELIVERING A SUBSTANCE

CROSS REFERENCE TO RELATED APPLICATIONS

This application is a continuation of Ser. No. 10/112,933 filed Apr. 2, 2002, which is herein incorporated by reference in its entirety.

FIELD OF THE INVENTION

The present invention is directed to a method and device for delivering a substance intradermally to a patient. The invention is also directed to a microneedle delivery device for containing and delivering a unit dose of a substance intradermally to a patient.

BACKGROUND OF THE INVENTION

Subcutaneous delivery devices using a cannula are effective for many applications. However, the pain normally induced by the cannula has prompted the development of less painful delivery methods. Recently, a number of intradermal devices employing microneedles have been designed. The microneedles have a length selected to penetrate the skin to a depth where a drug or pharmaceutical agent can be delivered to a patient.

In humans, the skin is made up of several layers, with the upper composite layer being the epithelial layer. The outermost layer of the skin, the stratum corneum, has well known barrier properties to prevent molecules and various substances from entering the body and analytes from exiting the body. Bouwstra, et al., (2001) Skin Pharmacol Appl Skin Physiol, 14 Suppl 1:52-62.

The stratum corneum is a complex structure of compacted keratinized cell remnants having a thickness of about 10-30 microns which forms a waterproof membrane to protect the body from invasion by various substances and from the outward migration of various compounds.

The natural impermeability of the stratum corneum prevents the administration of most pharmaceutical agents and other substances through the skin. Numerous methods and devices have been proposed to enhance the permeability of the skin and to increase the diffusion of various drugs through the skin to be utilized by the body. Typically, increasing either the permeability of the skin or the force or energy used to drive therapeutics through the skin enhances delivery of drugs through the skin. Bouwstra, et al., supra.

Another method of delivering various substances through the skin is by forming micropores or microcuts through the stratum corneum. By penetrating or piercing the stratum corneum and delivering a drug to the skin in or below the stratum corneum, many drugs can be administered effectively. The devices for piercing the stratum corneum generally include a plurality of micron-sized needles or blades having a length selected to pierce the stratum corneum without passing completely through the epidermis. Examples of these devices are disclosed in U.S. Pat. No. 5,879,326 to Godshall et al., U.S. Pat. No. 5,250,023 to Lee et al., and WO 97/48440.

The above-noted devices that include micron-sized needles or blades deliver the substances to the body by allowing the substances to flow through pores or channels in the device. Many of these prior devices do not provide a controlled delivery of a substance to the patient.

The prior methods and devices for the intradermal administration of substances have exhibited limited success. Accordingly, a continuing need exists for an improved device for administration of various drugs and other substances to the body.

SUMMARY OF THE INVENTION

The present invention is directed to a method and device for the delivery of a substance though the skin of a patient. More particularly, the invention is directed to a method and device for delivering a pharmaceutical agent, such as a drug or vaccine, below the stratum corneum of the skin to a depth at which the pharmaceutical agent can be absorbed and utilized by the body. The invention is further directed to a method of manufacturing and assembling a device for intradermally delivering a substance through the skin of a patient.

Accordingly, a primary object of the invention is to provide a low profile device to provide an increased comfort level to the patient, wherein the device has a skin penetrating member for introducing the substance to the patient.

A further object of the invention is to provide a device for penetrating the skin for delivering a unit dose of a substance through the skin substantially without pain to the patient.

Another object of the invention is to provide a device having at least one micro skin penetrator, (e.g., microtube, microneedle, microblade or lancet) for piercing the stratum corneum of the skin to deliver a substance to a patient.

A further object of the invention is to provide a delivery device having at least one skin penetrating member and a chamber for containing a substance to be delivered to a patient.

Still another object of the invention is to provide an intradermal delivery device having an indicator for indicating that a sufficient amount of a substance, for example, a premeasured dose, has been delivered from a chamber intradermally to a patient and an arrangement for producing a dispensing enhancing pressure in the chamber throughout the dispensing operation.

Another object of the invention is to provide a device for delivering a substance to a patient, wherein the device has a support with an internal supply channel having a very low dead volume and a micro skin penetrator device bonded to the support in fluid communication with the supply channel for delivering the substance to the patient.

A further object of the invention is to provide a delivery device having a plurality of micro skin penetrating members, wherein the device includes at least one elastic wall for producing a dispensing enhancing pressure in an internal chamber containing a substance to deliver to the patient and for indicating when a sufficient amount of the substance has been dispensed.

Another object of the invention is to provide an intradermal delivery device having an internal chamber with an arrangement for filling and pressurizing the internal chamber.

Another object of the invention is to provide for the intradermal delivery device a liquid source for supplying a liquid substance to the internal cavity by a force sufficient to pressurize the housing and produce the dispensing enhancing pressure throughout the dispensing operation.

A yet further object of the invention is to provide a method for intradermally delivering a substance to a patient comprising providing a delivery device which has a housing with an internal cavity and at least one skin penetrating device in fluid communication with the cavity, wherein the housing is pressurizable for maintaining a dispensing enhancing pressure in the cavity, the delivery device is positioned on a target area on the skin of a patient, and sufficient force is applied to cause the skin penetrating device to penetrate the skin of the patient. A substance is introduced into the cavity of the housing, the substance producing the dispensing enhancing pressure in the cavity.

These and other objects of the invention are substantially achieved by providing an intradermal delivery device comprising a housing having an internal cavity dimensioned to receive a substance for delivery to a patient, a skin penetrating device in fluid communication with the cavity, and a resiliently biased movable member in fluid communication with the cavity. The resiliently biased movable member produces a dispensing enhancing pressure in the cavity for dispensing the substance from the cavity to the skin penetrating member and indicates the delivery of a sufficient amount of the substance to the patient.

The objects and advantages of the invention are further attained by providing an intradermal delivery device comprising a housing having at least a portion made of an expandable material with sufficient elasticity to produce a dispensing enhancing pressure when the cavity is filled with a substance and to indicate that the cavity has not yet delivered a sufficient amount of the substance. A skin penetrating device is coupled to the housing and is in fluid communication with the cavity.

The present invention is directed to a device for delivering a substance into the skin of a patient. More particularly, the invention is directed to an intradermal delivery device and to a method for administering a substance below the stratum corneum of the skin of a patient where the substance is absorbed and utilized by the body.

As used herein, the term "penetrate" refers to entering an object, such as a layer of the skin, without passing completely through. The term "pierce" refers to passing completely through an object, such as a layer of the skin.

The device and method of the present invention are suitable for use in administering various substances, including pharmaceutical agents, to a patient, and particularly to a human patient. As the term is used herein, a pharmaceutical agent includes a substance having biological activity that can be delivered through the body membranes and surfaces, particularly the skin. Examples of pharmaceutical agents include antibiotics, antiviral agents, analgesics, anesthetics, anorexics, antiarthritics, antidepressants, antihistamines, anti-inflammatory agents, antineoplastic agents, vaccines, including DNA vaccines, and the like. Other substances that can be delivered intradermally to a patient include proteins, peptides and fragments thereof. The proteins and peptides can be naturally occurring, synthesized or recombinantly produced.

The delivery device of the present invention is constructed for penetrating selected layers of the dermis of a patient to attain the desired depth of penetration. The desired depth of penetration is determined by the substance being delivered and the desired rate of absorption by the body. Less penetration speeds the uptake of the substance by the body, and greater penetration slows delivery. It is contemplated that the skin penetrating member has a length of about 50 microns to about 1,500 microns. It is also contemplated that an array of such skin penetrating members can be used. The penetrating members have a length designed to pierce the stratum corneum without inducing pain by impacting nerve endings. By delivering a substance below the stratum corneum, the substance can be absorbed and utilized by the body substantially without pain or discomfort to the patient. Preferably, the skin penetrating members have a length and diameter to penetrate the skin to a depth where the patient experiences little or no pain, for example, below the stratum corneum and above the nerve endings.

The present invention is directed to an intradermal delivery device for delivering a substance into the skin of a patient where the device is able to maintain a dispensing enhancing pressure for delivering the substance. More particularly, the invention is directed to a unit dose delivery device for the sustained delivery of a substance through the skin of a patient.

The objects, advantages and other salient features of the invention will become apparent from the following detailed description which, taken in conjunction with the annexed drawings, discloses preferred embodiments of the invention.

BRIEF DESCRIPTION OF THE DRAWINGS

The following is a brief description of the drawings.

DETAILED DESCRIPTION OF THE PREFERRED EMBODIMENTS

Figure 1:
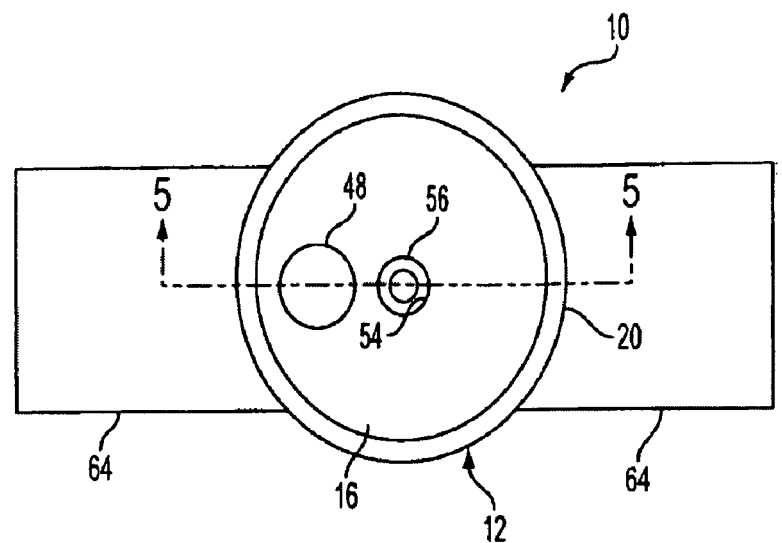
FIG. 1 is a top view of a delivery device in accordance with a first embodiment of the invention.
Figure 2:
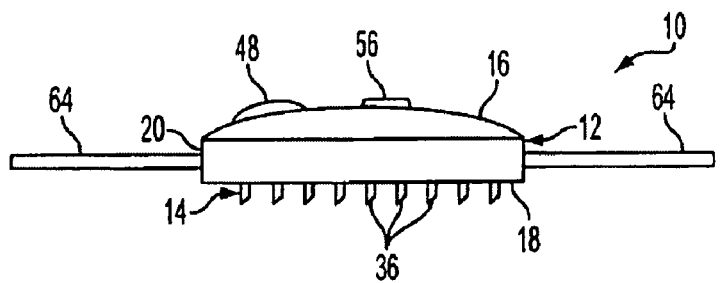
FIG. 2 is a front elevational view of the device of FIG. 1.

As can be seen from FIGS. 1-6, a first embodiment of a delivery device according to the present invention, which is designated generally by the reference numeral 10, comprises a housing 12 and a skin penetrating device 14. Housing 12 is dimensioned to contain a substance to be delivered to a patient and to be removably attached to the surface of the skin. Skin penetrating device 14 is associated with housing 12 to penetrate the skin of the patient and deliver the substance from housing 12 through the skin penetrating device 14. The present invention has both human and veterinary applications in delivering therapeutics across the stratum corneum. For example, canine and feline dermatology is similar to human dermatology with respect to the location and permeability of strata corneum. Moriello, K. A.; Mason, I. S., Handbook of Small Animal Dermatology, Pergamon, 1995, pp. 19-44.

The housing 12 has a substantially circular configuration, with a top wall 16, a bottom wall 18 and a side wall 20 extending between top wall 16 and bottom wall 18. Top wall 16, bottom wall 18 and side wall 20 define an internal cavity 22 of housing 12, as is shown in FIGS. 5 and 6.

Bottom wall 18 is substantially flat and is defined in part by the skin penetrating device 14, the bottom wall having a peripheral portion 23, including a central opening 24 for receiving skin penetrating device 14. The peripheral portion 23 of the bottom wall 18 surrounding opening 24 defines a ledge 26 extending beyond a receiving side wall 28, the ledge 26 and the receiving side wall 28 being dimensioned to receive skin penetrating device 14.

Figure 3:
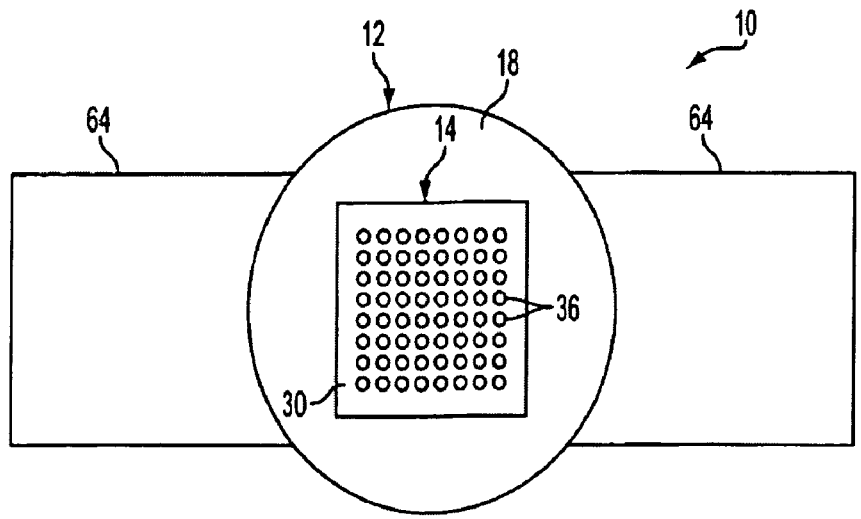
FIG. 3 is a bottom view of the device of FIG. 1, showing a skin penetrating device.
Figure 4:
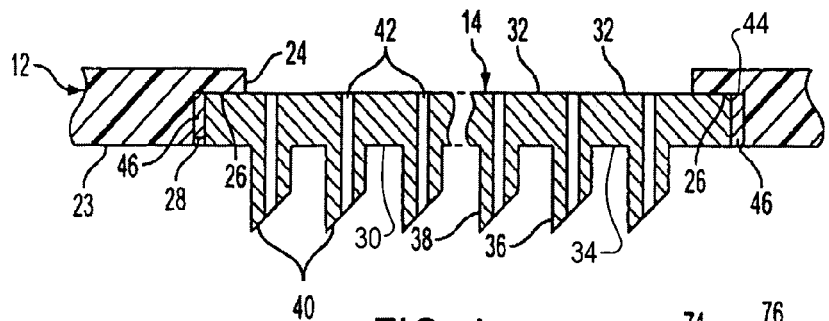
FIG. 4 is an enlarged partial cross-sectional view of the device of FIG. 2, showing the skin penetrating device 3 bonded to a housing.
Figure 5:
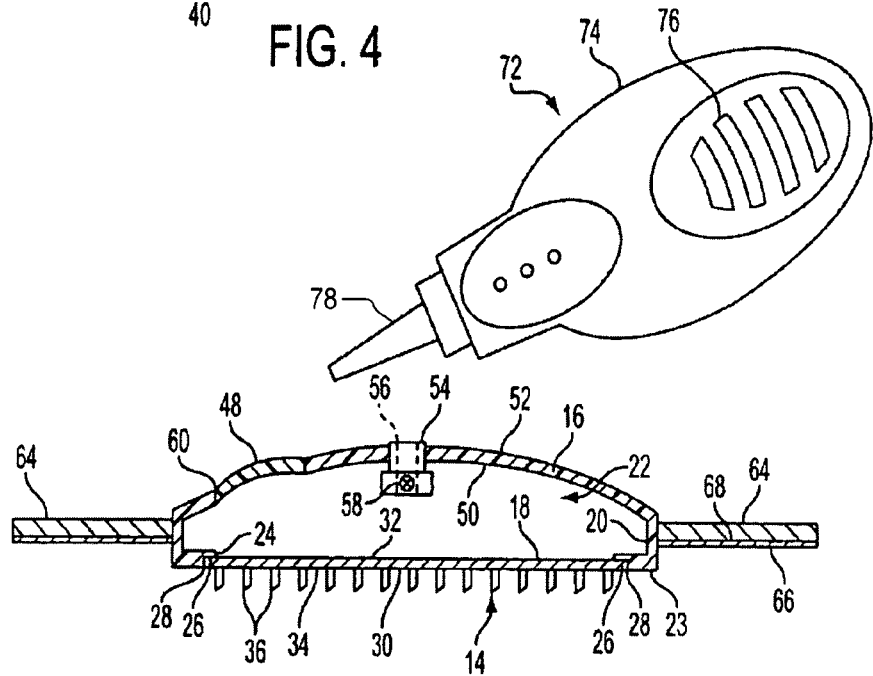
FIG. 5 is an enlarged cross-sectional view taken along the line 5-5 in FIG. 1, showing a cavity in the housing and a diaphragm in a normal, relaxed state.
Figure 6:
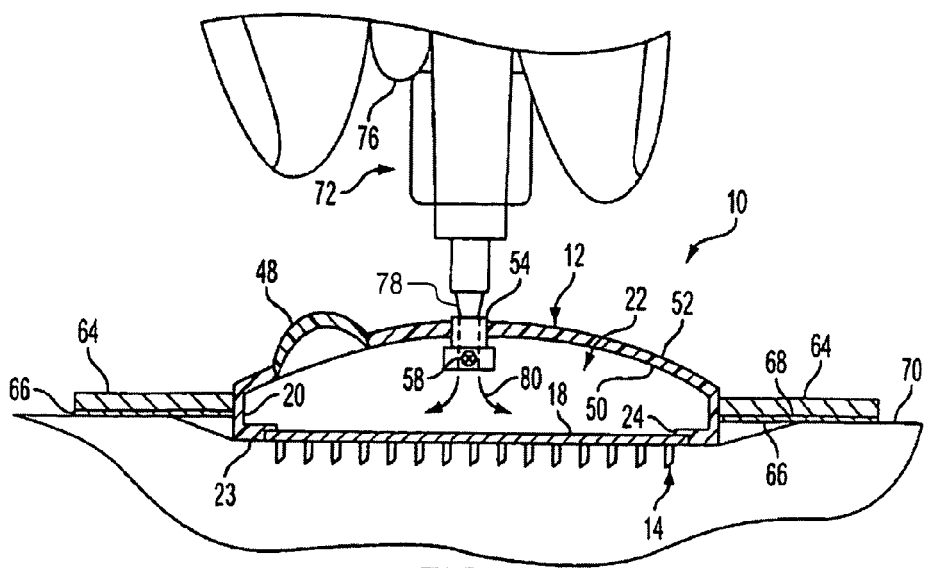
FIG. 6 is a cross-sectional view similar to FIG. 5 but showing the cavity filled with a substance and the diaphragm in a stretched state for producing an indication of an insufficient amount dispensed and a dispensing enhancing pressure.

The skin penetrating device 14 of the embodiment illustrated in FIGS. 1-6 has a microneedle array. As can best be seen from FIG. 4, skin penetrating device 14 includes a base 30 having a substantially planar top face 32 and a bottom face 34. A plurality of spaced-apart skin penetrating members 36 in the form of microneedles extend downwardly from bottom face 34. As is shown in FIGS. 4 and 5, the skin penetrating members 36 have a generally cylindrical side wall 38 and a beveled tip 40. An axial passage 42 extends through each of the skin penetrating members 36 from its beveled tip 40 to the top face 32 of the base 30. Axial passages 42 are in fluid communication with cavity 22 of housing 12. Typically, skin penetrating members 36 extend perpendicularly from bottom face 34 and are arranged in an array formed by spaced-apart rows and columns.

In a preferred embodiment of the invention, skin penetrating device 14 is coupled to bottom wall 18 of housing 12 so that bottom face 34 of the base 30 is in the same plane as the bottom surface of bottom wall 18 of housing 12. In other words, bottom face 34 of skin penetrating device 14 is flush with bottom wall 18 of housing 12. As is shown in FIG. 4, opening 24 in bottom wall 18 is slightly larger than the outer periphery of skin penetrating device 14 to define a small gap between the outer periphery of the skin penetrating device and the receiving side wall 28. Typically, skin penetrating device 14 is attached to bottom wall 18 by applying an adhesive 46 to fill the gap. Preferably, adhesive 46, which has a viscosity permitting the adhesive to flow around gap 44, can be cured to permanently couple skin penetrating device 14 to housing 12.

As can be seen from FIG. 3, skin penetrating device 14 has a substantially square base 30 that is centrally located in bottom wall 18 of housing 12. In alternative embodiments, base 30 of skin penetrating device 14 can have a generally circular shape or other shape. In a similar manner, circular is just one suitable shape for housing 12. Alternatively, housing 12 can have a substantially square or other rectangular shape or still other shape.

In preferred embodiments, housing 12 is pressurizable, the housing including a resiliently biased dispensing member 48 for indicating that a sufficient amount of a substance has been delivered from the cavity 22 to a patient and for providing a dispensing enhancing pressure to boost the delivery rate of the substance throughout the dispensing operation. The resiliently biased dispensing member 48 moves to a position in which a sufficient amount of the substance has been delivered, the presence of the member 48 in that position indicating that a sufficient amount of the substance has been delivered. In view of its indicating function, the resiliently biased dispensing member 48 is visible from the exterior of the delivery device 10. The top wall 16 has a generally concave inner face 50, a substantially convex outer face 52, and an arrangement for filling cavity 22 with a substance to be delivered to a patient. In the illustrated embodiment, the arrangement comprises a coupling member 54 having an inlet port 56 defining a passage in the coupling member 54 and a check valve 58 to allow a substance to be directed into cavity 22 while preventing leakage of the substance from cavity 22 out through inlet port 56. As an alternative, the arrangement can comprise a septum that is pierceable by, for example, the needle of a syringe, the septum being capable of resealing itself upon removal of the needle. Other arrangements can be used.

The resiliently biased dispensing member 48 is a resilient expandable member coupled to top wall 16 to close an opening 60 in the top wall. In preferred embodiments of the invention, the resiliently biased expandable dispensing member 48 is a diaphragm made from an elastomeric material that stretches when cavity 22 is filled under pressure and returns to its normal shape and dimension as the pressure is relieved. The elastomeric material has an area, thickness, and elasticity to provide a dispensing pressure sufficient to dispense a substance from cavity 22 through skin penetrating device 14 and into the patient. In moving from its pressurized position to its unpressurized position, the resiliently biased dispensing member 48 moves through a volume that is equal to the volume of the cavity 22 when the resiliently biased member is in its unpressurized position.

In the embodiment illustrated, the resiliently biased dispensing member 48 has a generally circular shape and is coupled to top wall 16. In alternative embodiments, the resiliently biased dispensing member 48 can have other shapes and dimensions depending on the dispensing requirements of device 10. In addition, dispensing member 48 can be coupled to a side wall. Examples of suitable materials for the dispensing member 48 are natural rubber and synthetic rubbers, such as polystyrene butadiene copolymers. The resiliently member 48 can be a separate member that is attached to housing 12 by a suitable adhesive, or it can be integrally formed with housing 12 the housing 12 and member 48 by molding as a single piece. Housing 12 is made from a rigid non-expanding material.

Device 10 is dimensioned to be applied directly to the surface of the skin of the patient in a manner such that skin penetrating device 14 penetrates the skin to the desired depth. The device 10 includes a flexible strip material 64 extending from opposite sides of housing 12. Strip material 64 is preferably a flexible polymeric film having an adhesive 66 on bottom face 68. Strip material 64 has a width slightly less than the diameter of housing 12 and a length sufficient to secure housing 12 to the surface of the skin of a patient. Typically, adhesive 66 is a pressure sensitive adhesive.

Device 10 is preferably constructed as a single use disposable item that can be made by a number of processes. Housing 12 is typically made from a polymeric material by suitable injection, vacuum or blow molding processes. In the embodiment illustrated, top wall 16, bottom wall 18 and side wall 20 are formed in one piece. As an alternative, housing 12 can be assembled from separate elements bonded together by an adhesive to form a fluidtight housing.

Typically, device 10 is manufactured and packaged in sterile conditions. The device 10 can be filled immediately prior to use with the substance to be administered, or it can be pre-filled. A cover can be applied over skin penetrating device 14 to protect the skin penetrating members and maintain the skin penetrating device in a sterile condition during storage. A suitable release sheet (not shown) is typically provided on adhesive layer 66. The release sheet and the cover can be removed immediately prior to use.

A method for delivering a substance intradermally to a patient using device 10 can be appreciated from FIG. 6. Device 10 is placed against the surface of the skin 70 of a patient and pressed downwardly against the skin until skin penetrating members 36 penetrate the skin. The depth of penetration is determined by the length, width and spacing of skin penetrating members 36. Insufficient spacing between skin penetrating members 36 causes increased skin resistance to the penetration of the skin penetrating members, a phenomenon sometimes called the "bed of nails" effect because some performers use it to enable them to lie on a hazardous looking bed of nails with no significant injury. Preferably, skin penetrating members 36 have a dimension and orientation to penetrate the surface of skin 70 substantially uniformly, as is shown in FIG. 6. In the embodiment illustrated, ends of the strip material 64 are coupled to the side wall 20 of the device 10 in an area spaced a slight distance from bottom wall 18 of housing 12. This arrangement maintains a slight downward pressure of housing 12 on skin 70 when strip material 64 is attached to skin 70, as is shown in FIG. 6. Alternatively, strip material 64 can be coupled to the side wall 20 at the bottom wall 18.

As can be appreciated from FIGS. 5 and 6, coupling member 54 is constructed to couple with a unit dose delivery device 72. For this purpose, coupling member 54 can include a Luer-type collar or a friction fit type coupling. The illustrated unit dose delivery device 72 includes an outer housing 74, a hinged actuating member 76 and a dispensing tip 78 having a Luer-type connector or other construction for mating with coupling member 54 in a fluid tight manner as shown in FIG. 6. Unit dose delivery device 72 also includes an internal bladder (not shown) in fluid communication with dispensing tip 78. By the use of the unit dose delivery device 72, the device 10 can be filled with a premeasured dose of a substance to be delivered to a patient. As a result, the resiliently biased member 48 again reaching its unexpanded or unpressurized position indicates that a premeasured dose has been delivered. One suitable unit dose delivery device is commercially available from Becton Dickinson Company under the trademark UNIJECT. Other unit dose delivery devices can be used instead.

Device 10 is positioned on the skin 70 of the patient, as can be seen from FIG. 6, and unit dose delivery device 72 is coupled to coupling member 54. Actuating member 76 is pressed inwardly to compress the internal bladder of the unit dose delivery device 72 and inject the substance contained in the bladder into cavity 22 of housing 12, as indicated by arrows 80 in FIG. 6. The substance is injected with sufficient force to expand the resiliently biased member 48 outwardly from top wall 16. Unit dose dispensing device 72 is then removed from coupling member 54, while check valve 58 prevents the escape of the substance from the device 10 through coupling 56. The elasticity of the resiliently biased member 48 maintains a dispensing enhancing pressure in cavity 22 to force the substance slowly through the axial passages 42 of skin penetrating members 36 into the skin of a patient where the substance can be utilized by the body.

The resiliently biased member 48 returns to its original shape and dimension as the substance is dispensed. The dimensions and elasticity of the resiliently biased member 48 determine the volume of substance that can be delivered and the rate of delivery of the substance to the patient. After a dose of the substance has been delivered to the patient, the resiliently biased member 48 has returned to its normal shape and dimension, thereby indicating that a sufficient amount of the substance has been delivered. Then the device 10 is removed from the skin of the patient and discarded.

Housing 12 is preferably made from a plastic material that is non-reactive with the substance being delivered to the patient. Suitable plastic materials include, for example, polyethylene, polypropylene, polyesters, polyamides, polycarbonates, and copolymers thereof.

Skin penetrating device 14 can also be made from materials known in the art to be suitable. The skin penetrating members 36 can be microneedles formed from a silicon wafer that is machined or etched to form the microneedle array. As an alternative, the skin penetrating members can be microneedles formed from any of stainless steel, tungsten steel, alloys of any of nickel, molybdenum, chromium, cobalt and titanium, and other non-reactive metals. As another alternative, the skin penetrating members can be microneedles formed from ceramic materials, glass or polymers. In further embodiments, skin penetrating device 14 can be defined by distinct skin penetrating members that are mounted in a suitable base.

The skin penetrating members 36 have a length suitable to achieve the desired depth of penetration in the skin. The length and thickness of the skin penetrating members are selected based on the substance being administered and the thickness of the skin in the location where the device is to be applied. The skin penetrating members can be microneedles, microtubes, solid or hollow needles, lancets and the like. Generally, the skin penetrating members 36 have a length of about 50 microns to about 1,500 microns, and preferably about 500 microns to 1,000 microns. In one embodiment, the skin penetrating members 36 comprise needles of about 30-gauge to about 50-gauge needles mounted in apertures formed in a base. The skin penetrating members 36 are fixed to the base 30, from which they extend outwardly to have an effective length of about 50 microns to about 1,500 microns. As an alternative to a circular cross section, the skin penetrating members 36 can have a substantially square cross-sectional shape. As other alternatives, the skin penetrating members 36 can be triangular, cylindrical, or pyramid-shaped or they can be flat blades.

The array of skin penetrating members 36 has a width and length sufficient to contain the number and size of skin penetrating members 36 necessary to achieve the desired result for depth of skin penetration and delivery or sampling rate. Where an array of skin penetrating members 36 is used, the area of the array is preferably about 1 cm.sup.2 to about 10 cm.sup.2.

Generally, when the device is used as a delivery device, a pharmaceutical agent or drug solution is introduced into the port 56 by a syringe or other fluid dispensing device. In alternative embodiments, a dried or lyophilized drug or pharmaceutical agent is provided in cavity 22, on the outer surfaces of the skin penetrating members 36, or in the axial passages 42 of the skin penetrating members. A diluent such as distilled water or saline solution can then be injected into cavity 22 to dissolve and reconstitute the drug or pharmaceutical agent. The drug or pharmaceutical agent is then delivered to the patient through microneedles.

Figure 7A:
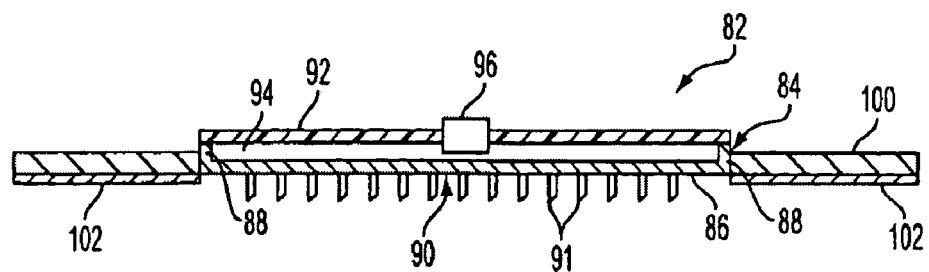
FIG. 7A is a cross-sectional side view of a delivery device in accordance with a second embodiment of the invention, wherein the device has an expandable diaphragm forming a top wall.
Figure 7B:
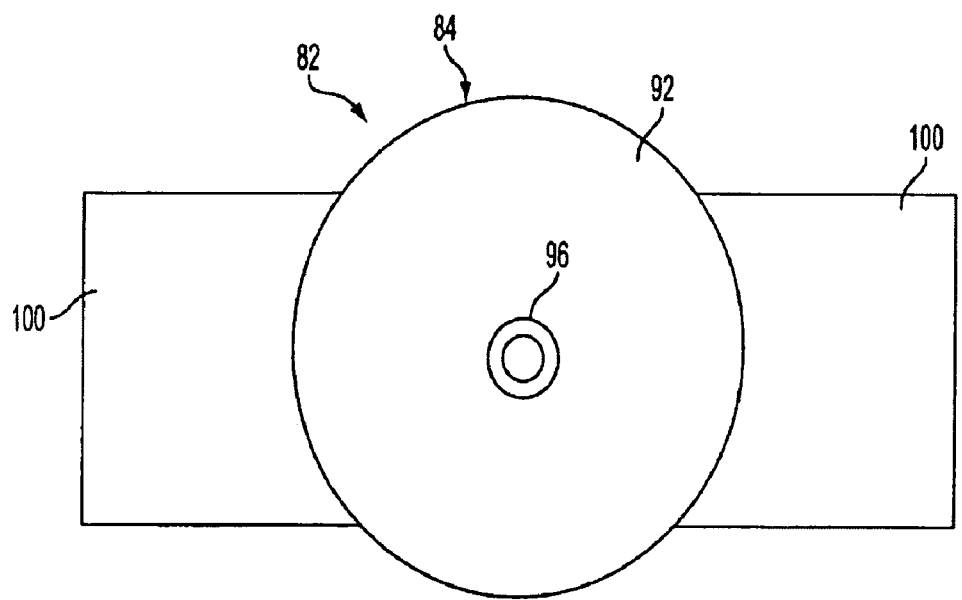
FIG. 7B is a top view of the device of FIG. 7A.
Figure 8:
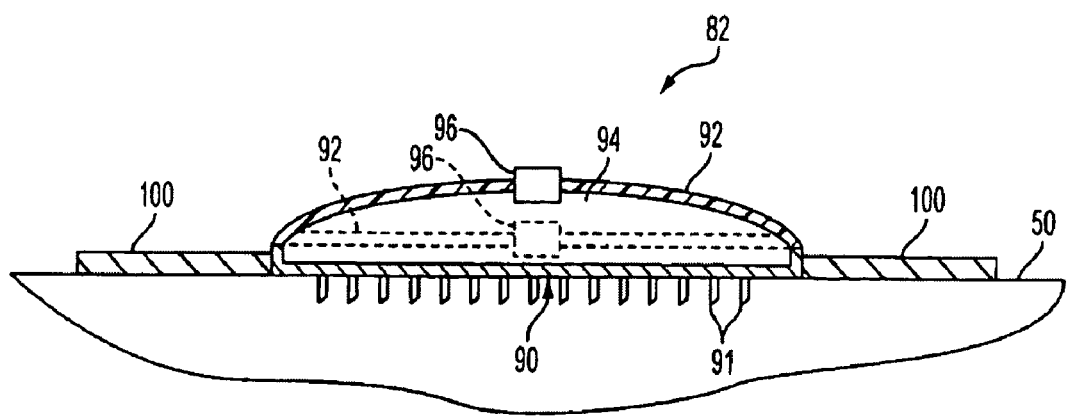
FIG. 8 is a cross-sectional side view similar to FIG. 7A but with the cavity filled with a substance and the diaphragm in the stretched state.

FIGS. 7A, 7B and 8 show another embodiment of the delivery device 82. In this embodiment, the delivery device 82 includes a housing 84 having a bottom wall 86 and side walls 88. A skin penetrating device 90 having a plurality of spaced-apart skin penetrating members 91 is coupled to bottom wall 86. A resiliently biased top wall 92 is connected to side walls 88 and spaced from bottom wall 86 to define an internal cavity 94. The skin penetrating members 91 can have all the various forms of the skin penetrating members 36 of the previously described embodiment for delivering the substance to the patient.

The top wall 92 is made from an elastic material that can stretch to enlarge cavity 94 when a substance is introduced into cavity 94 under pressure. As in the previous embodiment, top wall 92 includes a coupling member 96 having a through passage and an internal check valve, whereby coupling member 96 can be connected to a unit dose injection device, such as the unit dose injection device 72 shown in FIGS. 5 and 6. Bottom wall 86 and side wall 88 are preferably made from a rigid, non-expanding material.

As in the previous embodiment, the delivery device 82 includes a flexible strip material 100 having an adhesive coating 102. In the embodiment illustrated, strip material 100 is coupled to side walls 88 adjacent bottom wall 86 so that the bottom face of strip material 100 is in the same plane as bottom wall 86.

The delivery device 82 is placed on the surface of the skin 106 and pressed downwardly to enable needles 91 of skin penetrating member 90 to penetrate the skin to a selected depth. Strips 100 are attached to skin 106 by adhesive 102 to releasably secure device 82 in position. The unit dose injection device is then coupled to coupling 96, and a selected dosage of a substance is injected into cavity 94 under sufficient pressure to expand top wall 92 outwardly as shown in FIG. 8. The elasticity of top wall 92 creates a dispensing pressure sufficient to dispense the substance through skin penetrating device 90 into the skin where the substance can be absorbed and utilized by the body. The return of the top wall to its unexpanded position indicates that a sufficient amount of the substance has been delivered.

Figure 9:
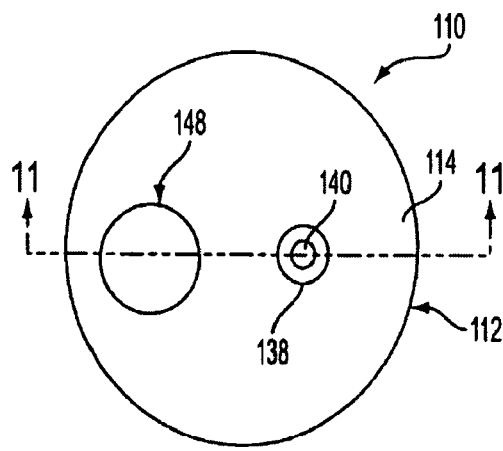
FIG. 9 is a top view of a delivery device in accordance with a third embodiment of the invention showing an inlet port and an expandable diaphragm in a top wall.
Figure 10:
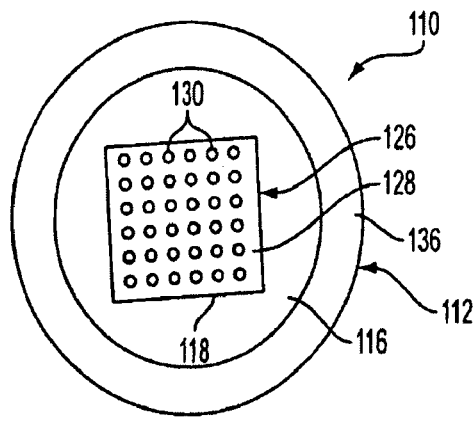
FIG. 10 is a bottom view of the delivery device of FIG. 9.
Figure 11:
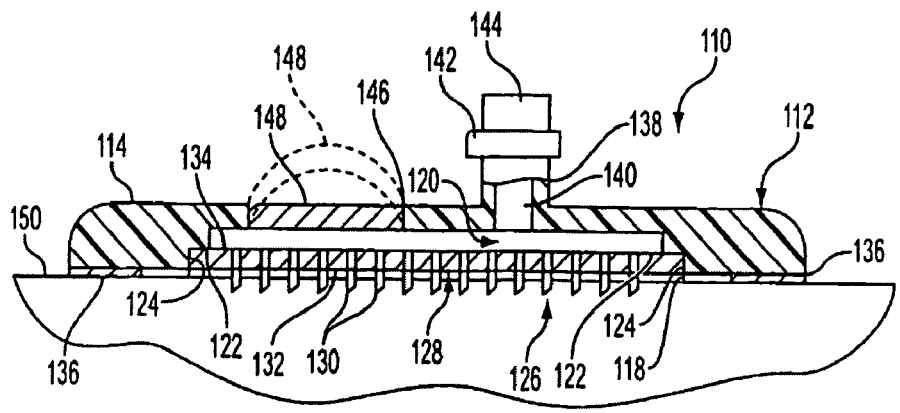
FIG. 11 is an enlarged cross-sectional view taken alone the line 11-11 in FIG. 9.

FIGS. 9-11 show another embodiment of a delivery device 110 according to the invention. The delivery device 110 includes a housing 112 having a top face 114, a bottom face 116 defining a recess 118, and a downwardly opening internal cavity 120. The recess 118 is defined by a ledge 122 and a perimeter wall 124 for receiving a skin penetrating device 126.

Skin penetrating device 126 includes a base 128 having a plurality of skin penetrating members 130, such as microneedles each having an axial through passage, extending outwardly from a bottom face 132 of base 128. Skin penetrating members 130 can be integrally formed with base 128 as in the previous embodiment. Alternatively, the skin penetrating members, 130 can be separate elements that are fixed in respective apertures in base 128. The base 128 has a thickness corresponding to the depth of the perimeter wall 124 so that bottom face 132 of the base is in the same plane as bottom face 116 of housing 112.

As can be seen from FIGS. 10 and 11, bottom face 116 has an area greater than the area of skin penetrating device 126 to provide a margin surrounding skin penetrating device 126. A pressure sensitive adhesive 136 is provided on the margin of bottom face 116 for attaching the delivery device 110 to the skin of a patient. Preferably, pressure sensitive adhesive 136 defines a continuous closed loop encircling skin penetrating device 126 and forms a seal around a delivering area on the skin contacted by skin penetrating device 126.

As can be seen from FIGS. 9 and 11, collar 138 having a central passage 140 communicating with cavity 120 projects above the top face 114 of the housing 112. A check valve 142 and a coupling member 144 are provided on collar 138. An opening 146 in top face 114 is closed by a resiliently biased member 148 connected to the housing 112 to seal cavity 120. The expanded position of the resiliently biased member 148 is indicated by the dashed lines in FIG. 1. The resiliently biased member 148 is preferably made from an elastomer capable of stretching and deforming outwardly from housing 112 and creating an internal dispensing enhancing pressure to helps dispense a substance from cavity 120 through needles 130 to the patient.

The delivery device 110 in the embodiment of FIGS. 9-11 has a relatively low profile and a small internal volume in cavity 120. The small internal volume reduces the dead space and minimizes waste of the substance that remains in housing 112 after the substance is delivered to the patient. Typically, housing 112 is made from a polymeric material that is sufficiently flexible to conform to the contours of the skin of the patient.

The delivery device 110 is placed against the surface of the skin 150 of a patient and pressed downwardly so that the skin penetrating members 130, such as microneedles, penetrate the skin. A substance to be delivered to the patient is introduced through coupling member 144 and central passage 140 into cavity 120 with sufficient pressure to expand the dispensing member 148 as indicated by the dashed lines in FIG. 11. The substance to be delivered to the patient can be introduced into cavity 120 from a unit dose injection device 72 or 98 as in the previous embodiments, or from a syringe, an infusion pump or other dispensing device. The dispensing device is then separated from coupling member 144 when a sufficient amount of substance is contained in cavity 120. The dispensing member 148 creates a dispensing enhancing pressure sufficient to force the substance through the skin penetrating members 130 into the skin of the patient. As the substance is delivered, the dispensing member 148 moves toward its unexpanded position and, by reaching that position, indicates that a sufficient amount of the substance has been delivered. After the substance has been delivered to the patient, device 110 is peeled from the surface of the skin and discarded.

Figure 12:
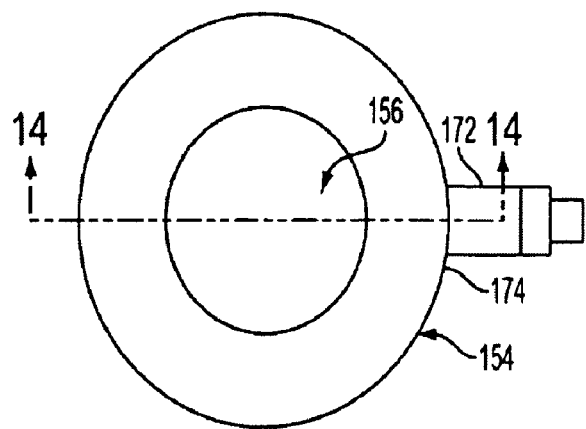
FIG. 12 is a top view of a delivery device in accordance with a fourth embodiment of the invention, showing an expandable top wall and an inlet port coupled to a side of a housing.
Figure 13:
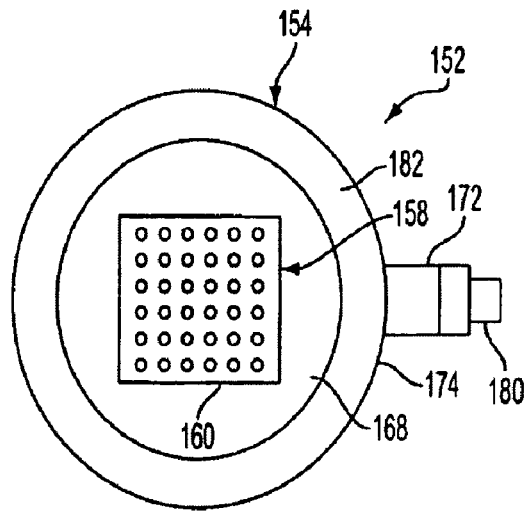
FIG. 13 is a bottom view of the device of FIG. 12, showing a microneedle array.
Figure 14:
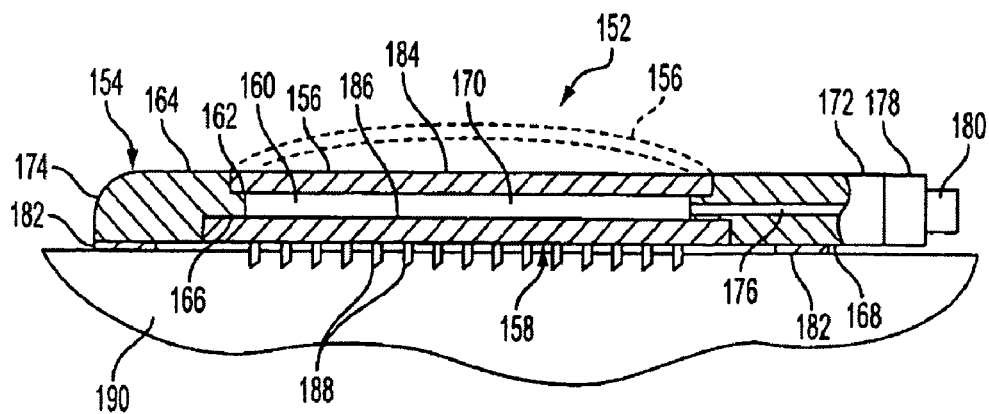
FIG. 14 is an enlarged cross-sectional view taken along the line 14-14 in FIG. 12, showing a microneedle array and an internal chamber.

FIGS. 12-14 show another embodiment of a delivery device 152 in accordance with the invention. The delivery device 152 includes a housing 154, an expandable dispensing member 156 and a skin penetrating device 158.

Housing 154 has a substantially circular configuration with a low flat profile and a central aperture 160 having a top ledge 162 adjacent a top surface 164. As is shown in FIG. 14, a resiliently biased member 156 is connected to top ledge 162 to close a top end of the aperture 160.

Housing 154 also includes a bottom ledge 166 in a bottom face 168 surrounding a bottom end of the aperture 160. Bottom ledge 166 defines a recess for receiving and mounting skin penetrating device 158 on housing 154. As is shown in FIG. 14, dispensing member 156 and skin penetrating device 158 are spaced apart to define with the housing 154 an internal cavity 170.

Housing 154 is provided with a coupling member 172 extending from a side face 174 of housing 154, in substantially the same plane as housing. Collar 172 includes an inlet port 176 defining an internal axial passage extending to the internal cavity 170, as well as a check valve 178 and a coupling member 180 for coupling with a supply device. The axial passage of the port 176 extends from coupling member 180 through a side 174 of housing 154 for communicating with the internal cavity 170.

Bottom face 166 of housing 154 has an area greater than the area of skin penetrating device 158. A pressure sensitive adhesive forming a continuous closed loop is applied to a margin 168 of the bottom face, encircling skin penetrating device 158. Preferably, adhesive 182 is applied to the margin 168 to cover a sufficient surface area to attach device 152 to the surface of the skin of a patient.

The resiliently biased member 156 is preferably an expandable member made from an elastomeric material. In the embodiment illustrated, the resiliently biased member 156 is an elastic diaphragm member 184 that expands outwardly from housing 154 when a substance is introduced to cavity 170 under pressure. The elastic properties of diaphragm member 184 are sufficient to produce a dispensing enhancing pressure in cavity 170.

As in the previous embodiments, skin penetrating device 158 includes a base 186 having a plurality of spaced-apart skin penetrating members 188, for example, microneedles. A method of delivering a substance intradermally to a patient using device 152 appreciated from FIG. 14. The delivery device 152 is placed against the skin 170 of a patient and pressed downwardly so that the skin penetrating members 188 penetrate the skin 190 and the adhesive 182 contacts skin 190 with sufficient force to attach device 152 to skin and form a continuous seal and between the device and the skin, all around skin penetrating device 158. A unit dose injection device, like the injection device 72 is connected to coupling 180 for introducing a substance into cavity 170 under sufficient pressure to expand the dispensing member 184 outwardly as indicated by the dashed lines in FIG. 14. The unit dose injection device is disconnected after cavity 170 is filled. The delivery device 152 is retained in contact with skin 190 for a sufficient time for the dispensing member 184 to dispense the substance from cavity 170 through the skin penetrating members 188 and into the skin of the patient. By again reaching its unexpanded position, the resiliently biased member 156 indicates that a sufficient amount of the substance has been delivered. The delivery device 152 can then be separated from skin 190 and discarded.

While various embodiments have been chosen to illustrate the invention, it will be appreciated by those skilled in the art that various additions and modifications can be made to the invention without departing from the scope of the invention as defined in the appended claims.

We claim:

1. An intradermal delivery device for delivering a substance to a patient, said device comprising:
    a housing having an internal cavity, said cavity being dimensioned to receive a substance for delivery to a patient;
    a skin penetrating device in fluid communication with said cavity; and
    an indicator having an indicating surface responsive to a pressure within said internal cavity, wherein said indicating surface indicates the delivery of a sufficient amount of the substance to the patient, wherein said indicator comprises an indicating member having at least a portion movable to a position in which a sufficient amount of the substance has been delivered, wherein the presence of the indicating member in said position indicates that a sufficient amount of the substance has been delivered and the movable portion of the indicating member is visible from the exterior of the intradermal delivery device when the movable portion is in said position.

2. The intradermal delivery device of claim 1, wherein said skin penetrating device comprises at least one skin penetrating member having a length of about 500 microns to about 1,000 microns and is a needle from about 30 gauge to about 50 gauge.

3. The intradermal delivery device of claim 1, wherein said housing further includes an inlet for passing said substance into said cavity.

4. The intradermal delivery device of claim 3, further comprising a check valve connected to said inlet for preventing the substance from leaving said cavity through said inlet.

5. The intradermal delivery device of claim 1, wherein said movable portion is resiliently biased to said position.

6. The intradermal delivery device of claim 5, wherein said indicating member comprises an expandable resilient member expandable from said position, the resilience of said expandable resilient member biasing said movable portion to said position.

7. The intradermal delivery device of claim 6, wherein said expandable member is expandable by introducing a substance into said cavity under pressure.

8. The intradermal delivery device of claim 6, wherein said expandable resilient member is integrally formed with said housing.

9. The intradermal delivery device of claim 8, wherein said expandable resilient member is made from an elastomeric material.

10. The intradermal delivery device of claim 9, wherein said housing includes a top wall and said top wall includes an opening and wherein said expandable resilient member closes said opening.

11. The intradermal delivery device of claim 6, wherein the expandable resilient member is a diaphragm.

12. The intradermal delivery device of claim 11, wherein said diaphragm is made from an elastomeric material.

13. The intradermal delivery device of claim 6, wherein the expandable resilient member comprises at least a portion of the internal cavity dimensioned to receive a substance for delivery to a patient.

14. The intradermal delivery device of claim 13, wherein said housing has a substantially non-expanding portion made from a substantially non-expanding material.

15. The intradermal delivery device of claim 14, wherein said substantially non-expanding portion comprises an inlet for supplying said substance to said cavity.

16. The intradermal delivery device of claim 15, further comprising a check valve connected to said inlet to prevent the substance from leaving the cavity through said inlet.

* * * * *